US006973371B1

(12) United States Patent  
Benouali

(10) Patent No.: US 6,973,371 B1  
(45) Date of Patent: Dec. 6, 2005

(54) UNIT DOSE COMPLIANCE MONITORING AND REPORTING DEVICE AND SYSTEM

(76) Inventor: Nadir Benouali, 2480 Sawmill Village Ct., Columbus, OH (US) 43235

( * ) Notice: Subject to any disclaimer, the term of this patent is extended or adjusted under 35 U.S.C. 154(b) by 0 days.

(21) Appl. No.: 10/963,688

(22) Filed: Oct. 13, 2004

(51) Int. Cl.[7] .............................................. G06F 17/00
(52) U.S. Cl. ..................... 700/244; 700/242; 221/2; 221/8; 221/15; 368/10; 235/385; 340/3.1; 340/5.92
(58) Field of Search ................. 700/231, 232, 700/236, 244; 221/2, 8, 15, 25, 26; 368/10; 235/385; 340/3.1, 5.92

(56) References Cited

U.S. PATENT DOCUMENTS

| | | | |
|---|---|---|---|
| 4,034,757 A | 7/1977 | Glover | |
| 4,223,801 A | 9/1980 | Carlson | |
| 4,429,792 A | 2/1984 | Machbitz | |
| 4,526,474 A * | 7/1985 | Simon | 368/10 |
| 4,616,316 A | 10/1986 | Hanpeter et al. | |
| 4,617,557 A * | 10/1986 | Gordon | 340/309.7 |
| 5,088,056 A | 2/1992 | McIntosh et al. | |
| 5,181,189 A * | 1/1993 | Hafner | 368/10 |
| 5,289,157 A | 2/1994 | Rudick et al. | |
| 5,313,439 A * | 5/1994 | Albeck | 368/10 |
| 5,408,443 A | 4/1995 | Weinberger | |
| 5,412,372 A * | 5/1995 | Parkhurst et al. | 340/568.1 |
| 5,625,334 A | 4/1997 | Compton | |
| 5,710,551 A | 1/1998 | Ridgeway | |
| 5,836,474 A * | 11/1998 | Wessberg | 221/25 |
| 5,852,408 A | 12/1998 | Christiansen et al. | |
| 5,871,831 A * | 2/1999 | Zeiter et al. | 428/76 |
| 6,082,544 A * | 7/2000 | Romick | 206/531 |
| 6,294,999 B1 * | 9/2001 | Yarin et al. | 340/573.1 |
| 6,335,907 B1 * | 1/2002 | Momich et al. | 368/10 |
| 6,401,712 B1 * | 6/2002 | von Schuckmann | 128/203.15 |
| 6,411,567 B1 * | 6/2002 | Niemiec et al. | 368/10 |
| 2004/0133305 A1 | 7/2004 | Jean-Pierre | |
| 2004/0148054 A1 | 7/2004 | Schwartz | |

FOREIGN PATENT DOCUMENTS

| | | |
|---|---|---|
| WO | WO 03/090663 A1 | 11/2003 |
| WO | WO 03/091945 A1 | 11/2003 |
| WO | WO 03/098175 A1 | 11/2003 |

* cited by examiner

*Primary Examiner*—Khoi H. Tran
(74) *Attorney, Agent, or Firm*—Sean M. Casey

(57) ABSTRACT

A unit dose medication compliance monitoring and reporting apparatus and system that includes a dispenser shell formed with dose compartments. A retainer sheet affixed to the shell seals each compartment and partially bursts upon dispensing. A sensor network and monitoring and reporting circuitry records dispensing times and determines an average time interval, which can be reported with other data on an integral data display. The system can thereby monitor and report patient compliance with prescription regimens. Additional data can be recorded and displayed for augmented patient compliance assistance and analysis, which data can include customized informational messages, telephone and other patient support contact information, unit doses dispensed and remaining, reminder alarms, identification data, prescription regimens, among other data. In myriad variations and alternative preferred configurations, the devices and systems have demonstrated efficacy in minimalist to complex monitoring and reporting applications ranging from routine prescription monitoring to detailed clinical trial assessments.

20 Claims, 4 Drawing Sheets

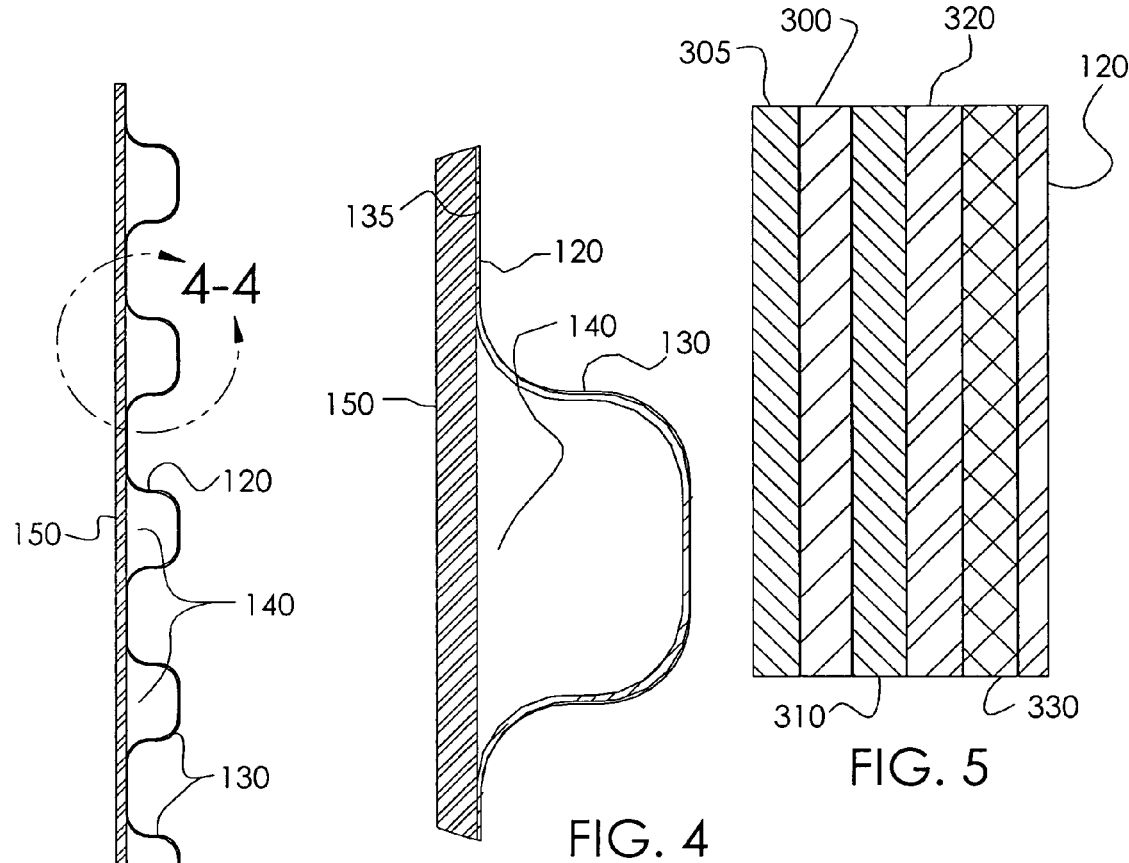
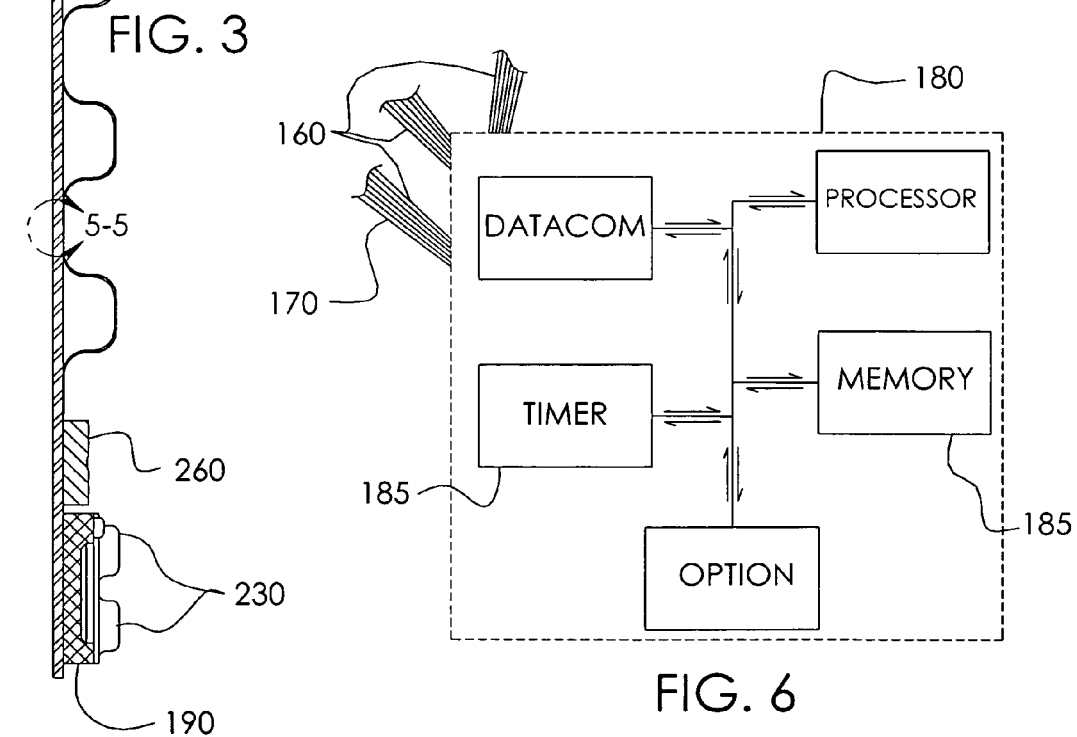

UNIT DOSE COMPLIANCE MONITORING AND REPORTING DEVICE AND SYSTEM

TECHNICAL FIELD

This invention spans several technology areas but is most often viewed to be in the field of pharmaceutical prescription, and sometimes over-the-counter, medicament compliance monitoring and reporting.

BACKGROUND OF THE INVENTION

A substantial amount of the costs associated with the treatment and management of medical conditions are devoted to prescribing and procuring pharmaceutical medications for consumption by patients. Even though best of class physicians and pharmacists can mediate a wide variety of medical conditions with appropriate pharmacological prescription regimens, sans hospitalization and controlled environments, obtaining the cooperative compliance of the target patient remains a key challenge.

Some experts seem to reason that de facto patient non-compliance with prescription regimens results in substantially increased burdens on medical professionals who must re-examine the patient, as well as unnecessarily increased pharmacological costs due to unused or improperly used medicaments that must be re-prescribed. Additionally, in the face of patient-asserted compliance, but apparent lack of clinical response due to de facto patient non-compliance with the originally prescribed regimen, such medicaments are most often replaced with alternative prescription regimens.

Many experts appear to agree that first-time patient compliance with prescription would unequivocally result in more effective amelioration of target medical conditions. In turn, enormous savings could be achieved with diminished burdens on medical professionals as well as the substantially reduced need to expend resources for re-prescribed or alternatively prescribed pharmacological products. The latter circumstance is perhaps understandably undesirable when viewed from the paradigm of the developers, manufacturers, and distributors of pharmacological products.

Over the last 2 or 3 decades, private, state, and federal health care insurers have become increasingly zealous in their efforts to control seemingly out-of-control costs. Of the many means by which they have sought to achieve such objectives, particular focus has been brought to bear on controlling the costs of pharmacological products. Such efforts have forced suppliers to find innovative ways to decrease costs.

Even so, health care insurers continue to search for every available means by which to decrease their costs, including trying to discover better methods to improve patient first-time compliance with prescription regimens so that repeat visits to medical professionals can be minimized. Improved first-time compliance by patients will also reduce if not eliminate the need to repeat prescriptions, and alternative prescription regimens for assertedly compliant, but de facto non-compliant patients that present lack of clinical response to the original prescription regimen.

Some attempts have been made in the past to address certain aspects of such issues. One purported medication compliance aid is described by Gordon in U.S. Pat. No. 4,617,557 wherein an improved unit dose blister package is disclosed. The Gordon '557 device is limited to a blister package that includes a reminder alarm that a physician or pharmacist sets when dispensing a prescription to a patient. Each time a unit dose is dispensed from the blister pack, the timer is reset and a reminder alarm sounds when the next dose is to be consumed by the patient.

In another application, Peterson et al. describe in Patent Cooperation Treaty Publication No. WO-03/090663 a concept that is restricted to a piezo-electrically actuated blister package that records the time each dose is dispensed for later downloading and analysis. An even more complex system is described by Jean-Pierre in U.S. Pat. Appl. No. 2004/0133305 A1, which is limited to a complex prescription drug compliance monitoring system that is restricted to use with wireless transmitters embedded into bottle-cap medicament containers.

While many attempts have been made, all such attempts are either expensive and cumbersome to implement and use, are limited in capability, or require doctor or pharmacist to patient interaction for purposes of monitoring or improving the prospects of patient compliance. While in the past, the doctor-patient or pharmacist-patient relationships have been the primary sources of influence that could motivate a patient to comply with the indicated prescription regimen most likely to achieve the desired clinical result, in more recent times, this paradigm has been demonstrated time and again to have less clinical effectiveness. Accordingly, the need for improved and more effective patient first-time compliance remains.

The instant invention and its many possible alternative preferred embodiments address many of the short-comings of the prior art that remain: cost to implement, ease of use, and the minimization of the probability that a patient will have an incentive to comply. The embodiments of the invention address these and many other prior art impediments with heretofore unavailable devices, systems, and methods. In particular, what has been needed and unavailable is an inexpensive to fabricate, reliable and easy-to-use, and cost effective means to greatly improve patient compliance without imposing undue complexity or onerous patient, doctor, or pharmacist burdens. The instant invention addresses such needs and accomplishes its new and novel improvements in the state of the art without adding any unacceptable costs or increased difficulties in the legacy prescription manufacturing, dispensing, and distribution systems and methods. Further, this is accomplished by taking advantage of the present-day relationships that now predominate in the industry. That is, the relationship between the patients and their respective health care insurance company. Most patients presently interact regularly with their insurer for purposes of obtaining reimbursements, for obtaining pre-approval for various medical services, as well as for a host of other necessary interactions.

In taking advantage of this existing relationship, burdens upon the expensive and limited medical professional resources can be attenuated. Further, since most individuals have only a single private or public health care insurer, the insurer can serve as a single repository of patient prescription compliance information. Additionally, patients are motivated to communicate with their insurer to be certain that they maximize their reimbursements for expenses, including reimbursement for their prescription medications. Even more importantly, the insurers are highly-motivated by commercial profit interests or public tax revenue limitations to control medication costs. Thus, more effective patient compliance controls can result in enormous cost savings, which in view of the instant invention are highly likely to far exceed any additional time and hard costs incurred in implementing the features and benefits of the instant invention.

SUMMARY OF INVENTION

In its most general configuration, the present invention addresses the problems in the art and advances the state of the relevant technology with a variety of new features and capabilities that innovate over and significantly improve prior devices in new and novel ways. In one of the many preferable configurations, the invention contemplates a unit dose medication compliance monitoring and reporting apparatus and system that includes, among other features and elements a dispenser shell and or a dispenser blister pack formed with unit dose compartments or containers, which can be formed like the blister packs well-known to those skilled in the relevant arts.

More preferably, the dispenser shell is formed with one side connoted to be a dispenser or an aperture face and with the containers or compartments defined with openings or apertures thereupon. Presently, both over-the-counter and prescriptions medicaments are increasingly being distributed to consumers in blister packages, which are available in single and multi-unit-dose arrangements of one, a few, to 7, 14, 28 dose arrangements, as well as configurations in higher quantities, including roll configured quantities that can be cut to size for automated packaging systems and centralized pharmaceutical dispensing operations such as those in hospitals and the like.

Further, the embodiments of the invention are directed to configurations that also incorporate a retainer sheet that is preferably affixed to the shell with adhesive or heat molding or sealing. In this way, each unit dose container or compartment, once filled with a selected unit dose of a desired or prescribed medicament, is thereby protected and sealed until use against inadvertent loss, or contamination from undesirable environmental stress, or from unwanted liquids, gases, or other debris. The phrase "unit dose" can have many meanings that can be understood by those having skill in the relevant arts. While not intending to limit the meanings of the "unit dose" term, one suitable meaning can include, solely for purposes of illustration and example, any amount of a medicament that is to be contained and dispensed in connection with the embodiments of the invention described herein and contemplated by the many modifications, variations, and alternative configurations of the preferred embodiments.

The retainer sheet is also preferably fabricated from any of a variety of materials that can enable dispensing of the unit dose by pressing the unit dose through the retainer sheet to thereby perforate or burst through the sheet. In many applications, it has been found to be effective to incorporate a score mark or partial scoring of an area of the retainer sheet that is about in the center of the container or compartment. Such scoring can reduce the pressure needed to dispense the unit dose as it is pressed through from the shell side of the assembled package. Thus, the perforation or bursting that is effected is more predictable in location and shape, and any pressure exerted on the unit dose to push it through the retainer sheet during dispensing is minimized.

In various of the preferred embodiments of the invention, a sensor network or networks and a monitoring and reporting circuit, circuits, and or circuitry is/are also included, which is configured to record dispensing times and or dates and to determine an average time interval between dispensing of unit doses. This average interval information, as well as detailed date and time dispensing data, can be reported with other data on an integral data display. Patient compliance with prescription regimens can thereby be monitored and reported. In variations of these configurations, additional data can be recorded and displayed as may be desired to enable assistance to the patient in his or her compliance efforts, and to augment post-compliance analysis by health care insurers, medical professionals, pharmacological product manufacturers, and support service providers.

Such enhanced information and data can include, for purposes of further example but not for purposes of limitation, customized informational text messages related to the medicament or treatment regimen, telephone and other patient support contact and assistance provider information, a count of unit doses dispensed and doses that remain, dose interval reminder alarms, medicament and patient and medical professional identification information, details related to the prescription regimen(s), and combinations thereof.

For purposes of the instant invention, the monitoring and reporting circuit, circuits, and or circuitry is/are preferably and optionally included as a modular subassembly or component group that can be attached during fabrication to the inventive unit dose medication compliance monitoring and reporting apparatus and system and device, and or optionally or preferably integrally formed as part of respective extended edges of the dispenser shell and retainer sheet assembly during fabrication. In either alternative configuration, the final assembled embodiments are operationally similarly capable and preferably functionally interchangeable. However, in the modular configuration, a detachable arrangement is contemplated that enables recycling of various of the monitoring and reporting circuitry, which may be optionally or preferably desirable for advanced applications such detailed monitoring of routine medicament prescription regimens, as well as clinical trials and the like where more comprehensive patient compliance information and feedback may be of import to the treating healthcare professional.

With these features and elements in mind, those having skill in the medical and pharmacological arts may be able to comprehend that the many modifications, variations, and alternative preferred configurations of the invention will be particularly useful even when used only in simplified forms for routine prescription monitoring. Even so, such effectiveness will only be amplified when the invention is used in more comprehensive and detailed monitoring and reporting applications such as in clinical trials of new medicaments and or treatment protocols requiring substantial patient and clinical controls and feedback.

In further contemplated improvements over previous devices, the preferred sensor network or networks can be arranged about the retainer sheet to have a plurality of frangible electrical container integrity signal paths or circuit traces or wires. Each path or trace or wire may be arranged or positioned to extend all the way or substantially across a respective opening when the retainer sheet is affixed to the dispenser sheet. In yet further variations of the preferred embodiments of the invention, the monitoring and reporting circuit may preferably be configured for electrical communication with integral and or separate timer and memory circuits.

In combination or separately and independently, the various circuits are preferably configured to record a time signal, which may also preferably and optionally include a date signal, each moment when a one of the frangible signal paths is broken or interrupted as the unit dose is dispensed. In yet further preferred variations and modifications and any of the preceding configurations, the monitoring and reporting circuit may also be configured to compute and record an average time interval signal of the recorded time signals and or date signals. In alternative arrangements and configurations of any of the preceding preferred and optional embodiments, the timer and or memory circuits may be similarly adapted to compute, store, and communicate the average time interval signal and dose dispensed and remaining signals in place of and or in tandem and combination with the monitoring and reporting circuit.

The inventive monitoring and recording device and apparatus may also incorporate a data display device, such as a liquid crystal or other type of electronic alphanumeric text and or graphics data display. In operation, the data display is arranged to be in electronic communication with the monitoring and reporting and other circuits. In this way, the data display is preferably adapted to communicate data with the circuits, and in most circumstances to display data there from. In even more preferred embodiments of any of the previously described modifications and configurations, the display can be adapted for automatic display of the average time interval signal of the recorded time signals, as well as other data that can include, for purposes of illustration without limitation, display of signals that represent the number of doses dispensed and yet to be dispensed.

The data display and or the various circuits incorporated into the novel monitoring and reporting device can also include one or more user data interfaces that can be implemented in the form of push-buttons, toggle switches, dials, and other types of switch devices. Even more preferably, the user data interface or interfaces can be in the form of substantially planar devices that can be incorporated into a substantially planar blister pack type of dispensing, monitoring, and reporting device according to the principles of the invention.

In commonly employed user data interfaces configurations of the invention, the switches will be operational to selectively adjust the data displayed in the limited space available in the form factor of the selected data display device. In one possible alternative configuration, the user data interface may be adapted with switches dedicated to scroll displayed data horizontally; in another, switches are dedicated whereby data can be scrolled vertically. In yet other additionally preferred configurations, the switches are reconfigurable to accomplish combinations of functions such as scrolling, and such as displaying other data for reporting that may be stored in the memory circuit or circuits. Such other data may include, for purposes of further example and illustration but not for purposes of limitation, any of the other types of described elsewhere herein and understood by those having skill in the art to be contemplated by the various embodiments and intended applications of the modified and alternative configurations of the preferred embodiments of the invention.

One particularly useful type of data to be communicated can preferably and optionally include an inbound report code that can be configured to uniquely identify the particular lot, manufacturer, unit dose medicament information, which can be communicated to a clearinghouse established and configured to capture that inbound report code. In this configuration, the inventive unit dose compliance monitoring and reporting device and system is well-suited to enable validation of patient compliance using the time interval signal for medical insurance reimbursement of costs, notification to manufacturers for analysis, among a host of other heretofore unavailable possibilities.

While many possible energy sources are contemplated for use with the devices of the invention, one preferred energy source for use in the invention can be what is commonly referred to by those skilled in the art as button type batteries. The battery can be inserted into the configurations of the invention either permanently or in a replaceable adaptation and can also be replaced or used in conjunction with a photovoltaic cell or solar battery. While the power consumption of the various preferred embodiments of the invention is very low, it may be also more preferable in various alternative arrangements to incorporate a power switch or to include an insulating tab to preserve battery life until the monitoring and reporting device and apparatus is issued to a patient for use, which will maximize battery shelf life.

In yet other alternative arrangements, the battery and or photovoltaic power source may be adapted to energize the various circuits only after the first unit dose of medicament is dispensed. In this configuration, the sensor network may incorporate a relay actuating shunt that de-energizes the circuitry until the first unit dose is dispensed and the trace or signal path triggers an energization relay or latch, which in turn energizes the device or apparatus. In consideration of the fact that the most commonly employed embodiments of the invention will include 1 to perhaps as many as 30 unit doses that would usually be dispensed within a couple of days to within a couple of months, the battery life of the most readily available button type batteries is deemed to be more than adequate for purposes of use with the variations and alternative configurations of the invention.

The various preferred configurations of the embodiments of the invention may also further incorporate any of a variety of possible signal path, wire, and or trace elements and technologies that can be used to fabricate the sensor network and other circuit paths and traces needed to establish the various monitoring and reporting and timer and memory circuits. One possible preferred arrangement that is contemplated includes what those skilled in the art often refer to as thin diameter, frangible bell wire that can be easily broken during dispensing of the unit doses as described herein. Yet other types of signal paths and traces can be used wherein electrically conductive materials are imprinted upon an insulating surface to establish frangible signal paths and or traces.

The preferred unit dose medication compliance monitoring and reporting devices and apparatus according to the principles of the invention may also further be directed to the retainer sheet being adapted with a one or more layers bound together or sandwiched against one another. The layers preferably include a sealing layer that is adapted to substantially prevent passage of liquids, gases, and solids to thereby protect the unit doses once the dispensing shell or blister pack is filled.

In addition, a conductor layer may be preferably or optionally included that is configured to be formed with or to receive the sensor network. Either integrally formed therewith or separately formed and affixed thereto, a metallic layer may also be included for various embodiments, which can be a foil sheet or other metallicized substrate desired or found to be suitable for purposes of the instant invention.

Even more preferably, any of the preceding preferred embodiments may also further include an insulative layer that can be incorporate between the metallic and conductor layers as may be needed for various operational configurations. In this latter alternative preferred arrangement, grounding bosses may be formed that establish electronic communication between, for illustrative example without limitation, the respective elements of the sensor network and the metallic layer, which can be used as a grounding conductor to eliminate the possible need for additional ground wires or traces or signal paths that may be required to complete the various circuits.

These variations, modifications, and alterations of the various preferred and optional embodiments may be used either alone or in combination with one another as can be better understood by those with skill in the art with reference to the following detailed description of the preferred embodiments and the accompanying figures and drawings.

BRIEF DESCRIPTION OF THE DRAWINGS

Without limiting the scope of the present invention as claimed below and referring now to the drawings and figures, wherein like reference numerals, and like numerals with primes, across the several drawings, figures, and views refer to identical, corresponding, or equivalent elements, components, features, and parts:

FIG. 3 is a section view, rotated and in modified scale and taken approximately about section line 3—3 of FIG. 1, of a portion of the unit dose compliance monitoring and reporting device and system of FIG. 1, with certain structure removed for purposes of illustration and example;

FIG. 4 is a detail view, rotated and in enlarged scale and taken about detail view line 4—4 of FIG. 3, and with certain components removed for purposes of illustration and example;

FIG. 5 is a detail view, rotated and in enlarged scale and taken about detail view line 4—4 of FIG. 3, and with certain components removed for purposes of illustration and example;

FIG. 6 is a diagrammatic detail view of a component of the unit dose compliance monitoring and reporting device and system according to the principles of the instant invention.

Also, in the various figures and drawings, various reference symbols and letters may be used to identify significant features, dimensions, objects, and arrangements of elements described herein below in connection with the several figures and illustrations.

DETAILED DESCRIPTION OF THE INVENTION

Figure 1:
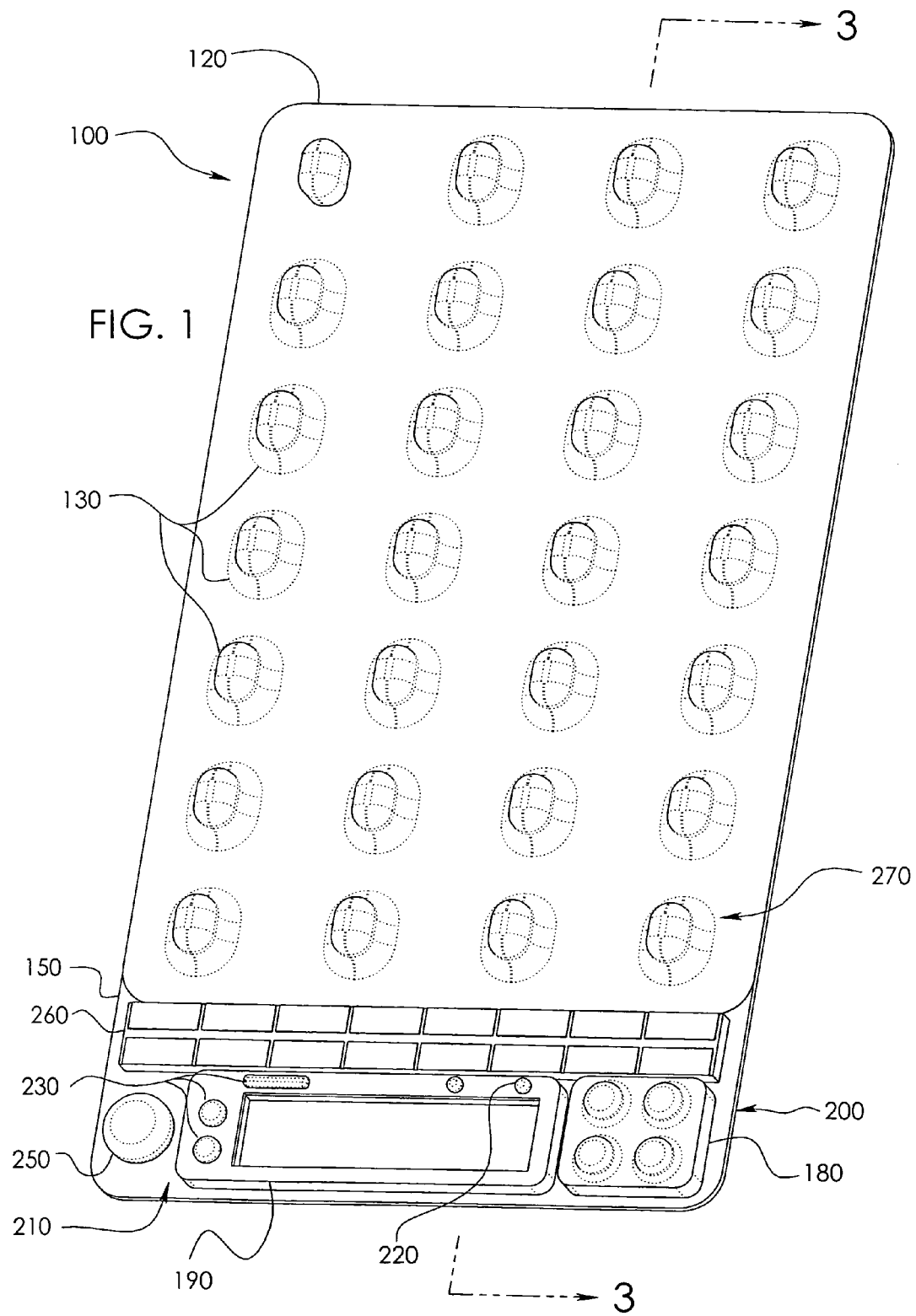
FIG. 1 is an isometric view, in modified scale, of one possible preferred embodiment of the unit dose compliance monitoring and reporting device and system according to the principles of he instant invention.

In a wide range of possible embodiments and modifications and variations thereof, the heretofore unavailable unit dose medication compliance monitoring and reporting apparatus and system according to the principles of the invention is denoted in general in the various drawings and in FIGS. 1 and 3 by reference numeral 100. Those having any skill in the art of pharmaceutical medicament dispensement blister package technologies, such as that taught in U.S. Pat. No. 4,429,792, which is incorporated by reference in its entirety, should be able to comprehend that a variety of possible blister type package configurations are suitable for use with and contemplated by the instant invention.

If appropriately skilled in the related fields of technology and art, interested individuals may be able to readily comprehend that the unit dose medication compliance monitoring and reporting apparatus 100 according to the principles of the instant invention can be manifested in a variety of configurations that include injection molded polymeric materials formed with conventional blister packaging methodologies, such as those described in the '792 patent, among others known to those skilled in the relevant arts.

What is termed here as a dispenser shell and or a dispenser blister pack 120 is preferably formed with unit dose compartments or containers 130. This type of shell or blister pack 120 can be selected from a widely used polymeric and or thermoplastic material injection molded and or thermoformed sheet material such as a polyethylene, polypropylene, or polytetrafluoroethylene (PTFE) plastics, which can have thicknesses in the range of about 0.003" or 0.005" to about 0.009", and even more preferably about 0.008". In other words, such preferred and optional configurations can range between from about 3 to 5 thousandths of an inch to about 9 thousandths, which units are also referred by those skilled in the art as "mils".

Those having skill, experience, and expertise in the relevant arts, should understand that the various preferred embodiments and alternative configurations of the invention are described here for purposes of example but not for purposes of limitation to have a configuration adapted to dispense 28 units doses. However, the many new, novel, and inventive aspects of the instant unit dose compliance monitoring and reporting device and system 100 are susceptible for use in myriad other configurations and modified alternative embodiments wherein more and fewer unit doses may be arranged for dispensement. Further, although the unit dose compartments and containers 130 of the device and system 100 are described in the written description and illustrative drawings and figures to define a generally ovoid shape, the metes and bounds of the instant invention are not intended to be limited to such a configuration. Instead, the many possible configurations of the preferred and optional embodiments of the invention can include such containers and compartments 130 being adapted to be received with single and multiple unit doses of medicaments that can be, for purposes of example without limitation, multi and single pill or tab form factor medicaments having any possible shape and size. In one possible, the unit doses of medicaments to be dispensed can include 2 capsules and one tab that together form a single unit dose, which is often employed in prescriptions issued for autoimmune-deficiency pharmacological therapies and chemotherapies.

More preferably, the dispenser shell or pack 120 is formed with one side connoted to be a dispenser or an aperture face 135 (FIG. 4) and with the containers or compartments 130 defined with openings or apertures 140 thereupon. A single and or multilayer retainer sheet 150 is also incorporated into the compliance monitoring and reporting devices of the instant invention 100, which can be preferably or optionally affixed to the shell or pack 120 with adhesive or heat molding or sealing or ultrasonic and infrared plastic welding technologies known to those skilled in the relevant arts.

For improved dispensement of the unit doses, the retainer sheet 150 may be adapted to incorporate a pre-scored or slotted aperture control groove 155 (FIG. 2), which can be formed in the sheet 150 to lessen the force needed to dispense the unit dose through the retainer sheet 150. Without such a pre-scored or through slotted aperture control groove 155, significantly increased force is required to dispense the unit dose, which can cause damage to the unit dose during dispensing. In place of or in combination with the control groove 155, a through hole can also be incorporated on the retainer sheet 150 to further improve ease of use during operation.

As can be understood with continued reference to FIG. 1, as well as also now to FIGS. 2, 3, 4, and 5, any of the preferred embodiments of the device and apparatus 100 can further incorporate a dispensement sensing or sensor network or networks 160, which establish(es) a circuit, circuits, and or circuitry that can be received upon, proximate or adjacent to and or integrally formed upon the retainer sheet 150 to have a plurality of frangible electrical container integrity signal paths or circuit traces or wires 170, each wire or trace or path 170 being positioned to substantially extend across a respective opening 140 when the retainer sheet 150 is affixed and attached to the shell or pack 120 after assembly.

Figure 2:
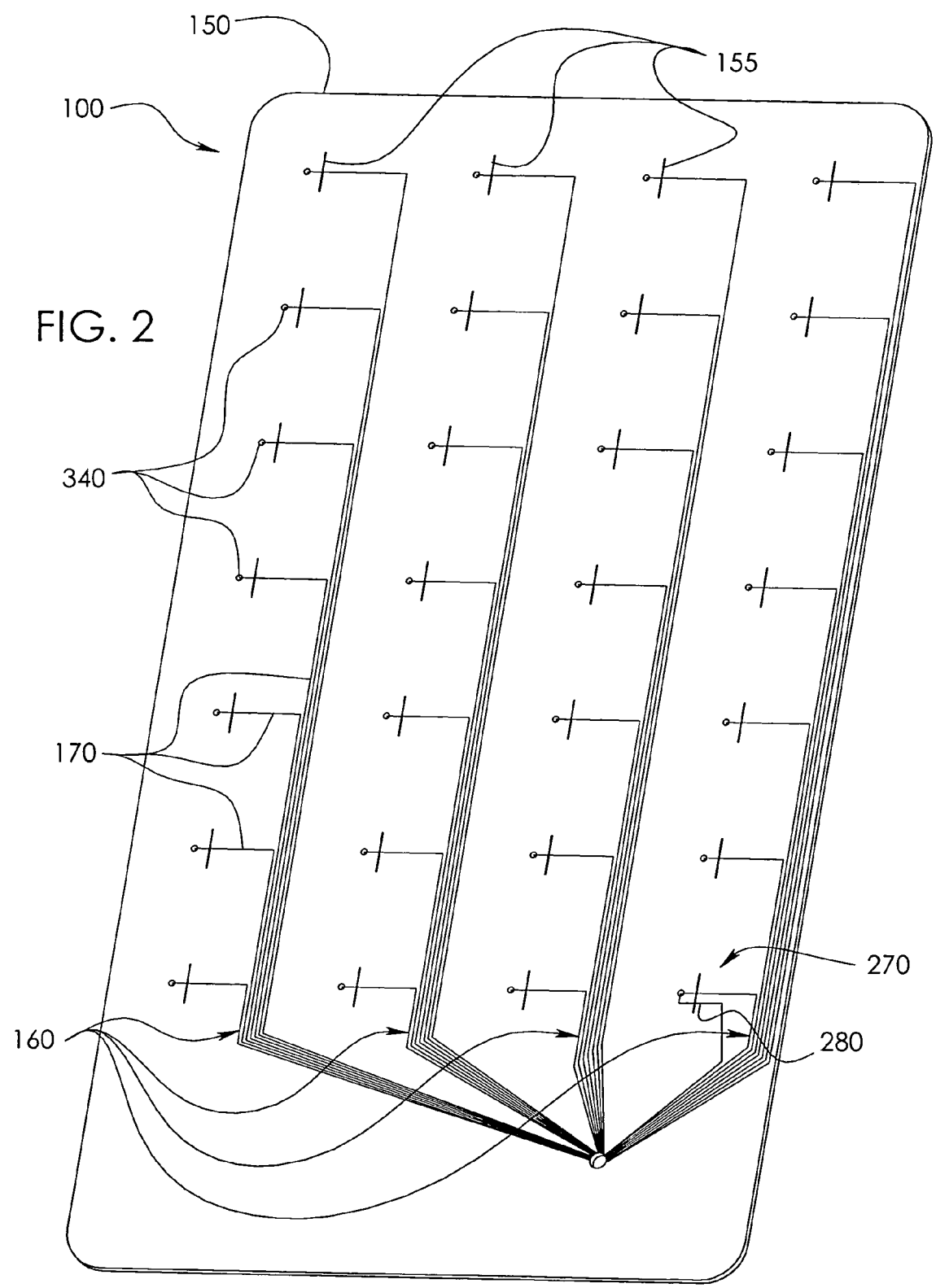
FIG. 2 is an isometric view, in modified scale and rotated, of a component of the unit dose compliance monitoring and reporting device and system of FIG. 1.

The inventive unit dose compliance monitoring and reporting device or pack 100 also further preferably includes a monitoring and reporting circuit 180 in electrical communication with timer and memory circuits 185 that are depicted diagrammatically in FIG. 6. As those skilled in the relevant arts may be able to further understand, the circuit 180 is configured to and or cooperates with circuits 185 to generate and record a time signal, and or date signal and or a combination thereof. Recordation is effected at each instance when a one of the frangible signal paths 170 is broken and interrupted as the unit dose, not shown but to be inserted and received during manufacture in the recess, container, and compartment 130 (FIG. 2).

In optional and preferred variations to any of the preceding configurations of the instant invention, the device or blister pack 100 also further includes a data display device 190 in electronic communication with invention, the monitoring and reporting circuit 180. The data display 190 is operationally configured to communicate data there from for display and visualization by a user. Although the various circuitry 180, and or the timer and memory circuits 185 can be integrally carried from the device or blister pack 100, the circuitry 180 may also be formed upon or carried from the shell or pack 120 and the retainer sheet 150, and or the assembly thereof 100.

Even further optional and preferred modified embodiments are contemplated wherein the monitoring and reporting circuit, circuits, and or circuitry 180, 185 is/are also configured to identify, count, and record dispensing times and or dates of the unit doses and to determine an average time interval between dispensing of unit doses. This average interval information can be reported with other data on an integral data display 190.

In any such configurations and alternative arrangements thereof, the monitoring and reporting circuit, circuits, and or circuitry 180, 185 may preferably and optionally be fabricated for attachment to the inventive unit dose medication compliance monitoring and reporting apparatus 100 about respective extended edges 200 (FIG. 1) of the dispenser shell or pack 120 and retainer sheet 150 assembly during fabrication.

With continued reference to FIG. 1, skilled individuals knowledgeable in the relevant arts may further come to appreciate that the data display 190 and or the various circuits 180, 185 that are contemplated for use with the inventive compliance monitoring and reporting device and blister pack 100 may further incorporate one or more user data interfaces 210 that can be implemented in the form of push-buttons 220, 230, toggle switches, dials (not shown), and other types of switch devices known to those skilled in the electronics arts.

The preferred and optionally preferred and alternative embodiments and configurations of the compliance monitoring and reporting device and blister packs 100 practiced in accordance with the principles of the instant invention also further contemplate various types of power sources that can include conventionally known button type batteries, such as battery 250 (FIG. 1) as well as a photovoltaic cell or solar cell 260, which devices can be used alone or in combination as depicted here. When used in combination, the solar cell 260 can be employed to recharge the battery 250 in certain preferred or optional arrangements.

In additionally preferred and optional variations to any of the preferred configuration already described, the battery 250 and or photovoltaic power source 260 may be adapted to energize the various circuits 180, 185 only after a first unit dose 270 of medicament is dispensed. In this alternative modified configuration, the sensor network 160 may incorporate a relay actuating shunt 280 (FIG. 2) that operates to de-energize the sensor network 160 and circuitry 180, 185 until the first unit dose 270 is dispensed. Further, the trace or shunt signal path 280 can be optionally or preferably configured to trigger an energization relay or latch (not shown but incorporated as part of the various circuits 180, 185).

With continued reference to the various figures and also specifically to FIG. 5, in yet further preferred and optional modifications and variations to any of the preceding embodiments, the retainer sheet 150 is also directed to configurations adapted with a one or more layers 300, 305, 310, 320, and 330 bound together or sandwiched against one another. Preferably or optionally included can be a sealing layer 330 that seals against the face 135 of the blister pack 120 (FIG. 4) to completely and or substantially seal against passage of liquids, gases, and solids. A conductor layer 320 may also be further preferably or optionally incorporated to be formed with, to carry, to sandwich, and or to receive the sensor network 160. Either integrally formed therewith or separately formed and affixed thereto, a metallic layer 300 may also be included for various embodiments, which can be a foil sheet or other metallicized substrate as already described herein elsewhere. Even more preferable embodiments can incorporate a paper layer 305 affixed to the outermost layer in the stack of possibly preferred and optional layers that is opposite from the face 135. The additional paper layer can be better adapted to receive imprinted indicia such as bar codes, manufacturer and product identification information, and other possibly desirable indicia. Further the paper layer 305 can be further adapted to impart increased strength to the layer stack as a child protective, tamper evidencing, and containment improvement element that will increase the force needed to push the medicament through the various layers for dispensement. Such indicia and bar codes and other optically readable data can also be imprinted directly on or on a paper layer affixed to the plastic shell 120 for ease of inventory, tracking, package identification, and dispensing.

Even more preferably, any of the preceding preferred embodiments may also further include an insulative layer 310 contemplated to be sandwiched between the conductor or conductive layer 320 and the metallic layer 300. In these alternative configurations and variations, grounding bosses 340 (FIG. 2) may be formed that establish electronic communication between the traces or signal paths 170 of the sensor network 160 on the conductor layer 320, and the metallic layer 300.

With continued reference to the various figures and FIG. 6, those skilled in the art should also comprehend that the instant invention also contemplates further modifications and alternative arrangements of any of the embodiments of the invention whereby the monitoring and reporting circuit 180 and or the timer and memory circuits 185 can be optionally or preferably modified to incorporate wired and wireless data communications, or datacomm, features and components as well as other options that can include serial communications interfaces, among other possibilities. In further possibly preferred and optional alternative embodiments, the monitoring and reporting circuit 180 and or the timer and memory circuits 185, although shown as separate components in the various figures and illustrations, can be integrated with one another and incorporated as a single component or single module on the unit dose compliance monitoring and reporting device and system.

With continued reference to FIGS. 1, 3, and 6, those having skill and expertise in the relevant arts should be able to comprehend that one such suitable internal electronic programmable processor and memory circuit 185 can be fabricated from what is commonly referred to in the industry as a PIC 877 single chip type computer system. Many manufacturers and suppliers across the world offer a variety of such PIC 877 units. Many other equally preferable single-chip-type and other types of processors and memory circuits and chips and computers are also available and can include, for purposes of example without limitation, what are known in the electronics and computer industries as the Basic Stamp series of computers from Parallax, Inc., and the 8051 series computers from Intel Corp. and Philips Corp., and many variants thereof are available from a host of domestic and international manufacturers.

Additionally, while a wide variety of possible and preferable non-volatile memory storage options are equally suitable for purposes of the instant invention, one inexpensive but reliable and well-suited memory storage component can include the Atmel Corp. 28-pin, 16M bit density, AT45 DB161B DataFlash® Serial-Interface Flash memory chip. Those skilled in the related art may also be able to comprehend that many possible data and programming interfaces are available and can include serial, Ethernet, parallel, infrared, wireless, radio, optical, and wired communications interfaces and wireless emitters and receivers and other means of communicating data are compatible for use with and contemplated for incorporation in the devices of the instant invention. Additionally, commonly used universal serial bus ("USB") components are also well-suited for communicating data to and from the device and system 100.

Figure 7:
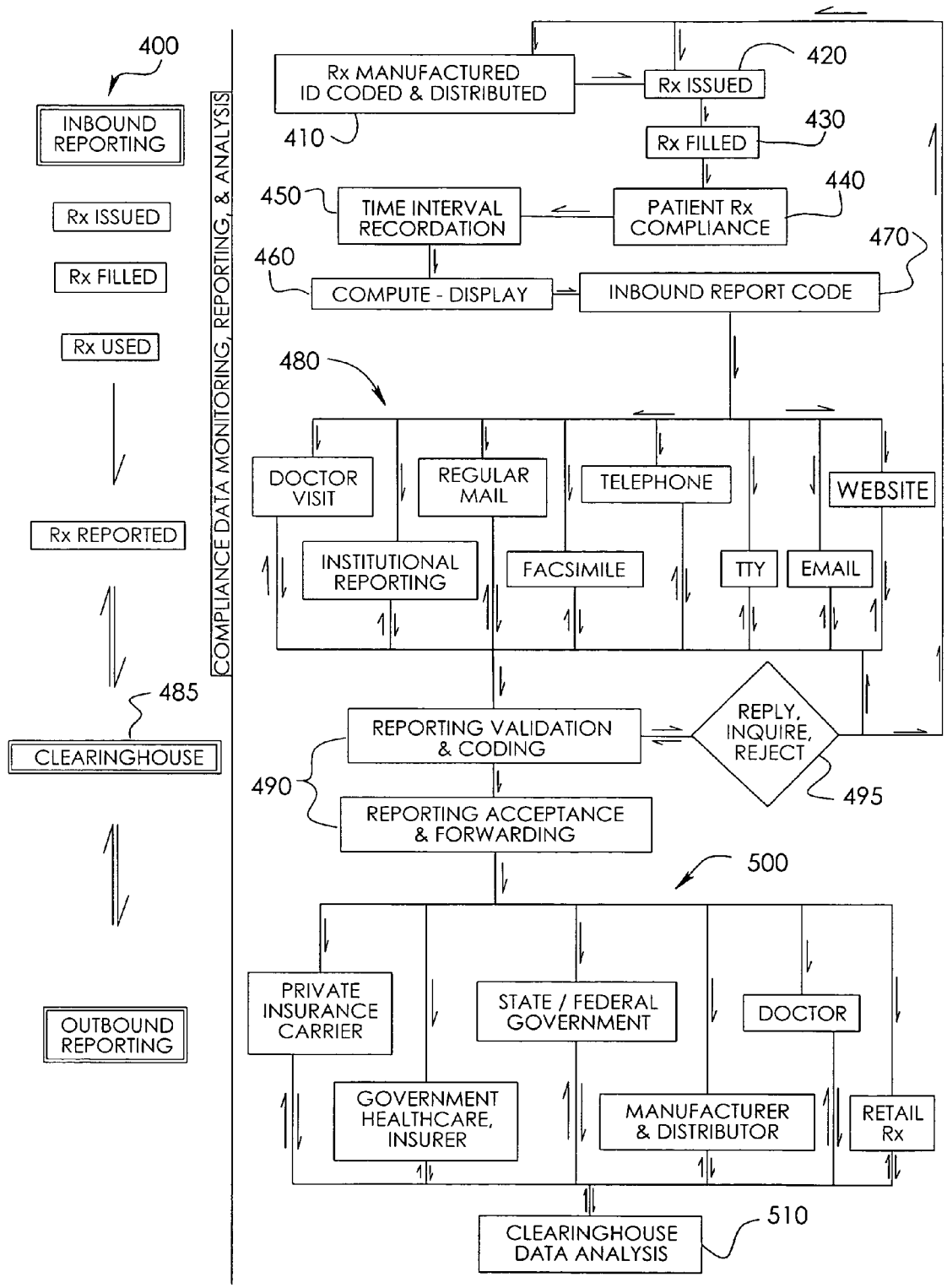
FIG. 7 is a diagrammatic data flow schematic that describes additional features, modifications, and variations of the unit dose compliance monitoring and reporting device and system of the invention.

In combination with the various additional capabilities described in, for example without limitation, the various modules of the system of FIG. 7, patient compliance with prescription regimens can thereby be monitored and reported. In variations of these configurations, additional data can be recorded and displayed as may be desired to enable assistance to the patient in his or her compliance efforts, and to augment post-compliance analysis by health care insurers, medical professionals, pharmacological product manufacturers, and support service providers.

Such enhanced information and data can include, for purposes of further example but not for purposes of limitation, customized informational text messages related to the medicament or treatment regimen, telephone and other patient support contact and assistance provider information, a count of unit doses dispensed and doses that remain, dose interval reminder alarms, medicament and patient and medical professional identification information, details related to the prescription regimen(s), and combinations thereof.

With continued reference to the various figures and now also specifically to FIG. 7, those skilled in the various arts may further comprehend additionally contemplated embodiments of the invention and alternative configurations and modifications thereto that are specifically enabled for compatibility with multi-tier unit dose monitoring and reporting compliance devices and systems 400. In one such exemplary alternative embodiment of the invention, the unit dose monitoring and reporting device and system 100 is fabricated with automated circuitry 180 and programming for inbound reporting of patient compliance data to a clearinghouse, which in turn validates the data for outbound reporting to various entities with a vested interest in patient medicament compliance.

For purposes of additional examples, but not for purposes of limitation, the alternatively configured unit dose monitoring and reporting device and system 100 is fabricated by a pharmaceutical manufacturer for controlled or prescription ("Rx") use and is coded with imprinted, embossed, or electronically encoded medicament, manufacturer, lot, and other optionally or preferred desired identification ("ID") data 410. The prescription Rx is then eventually issued 420 by a health care professional, which is filled 430 by a retail or institutional (hospital, hospice, long-term care facility) pharmacological dispensary.

Thereafter the unit dose monitoring and reporting device and system 100 is used by the patient who is required to comply 440 with the prescription to maximize health benefits and to diminish the otherwise inevitable lack of clinical results. As a possible means to save insurance costs, reimbursement of the prescription cost can be preferably tied to reported compliance within predetermined constraints that are adapted to comply with legacy rules and procedures to minimize detrimental impact to the medicament consuming patient.

In operations, the unit dose monitoring and reporting device and system 100 is used to dispense unit doses of medicament from the blister pack 120, wherein a dispensement count, time interval and or date of dispensement 450 is automatically identified, monitored, and recorded or captured by the device 100. Upon complete consumption of the prescribed unit doses of the medicament, which is deemed to be the desired compliance by the patient, the unit dose monitoring and reporting device and system 100 computes the average time interval 460 from the monitoring times and dates between dispensements of the unit doses, or some other compliance probative time/date data, and displays the data for compliance reporting purposes.

In even more preferred variations of any of the preceding embodiments of the invention, the average time interval 460 is selected to be a 4 digit number that represents minutes, which can be displayed for review by the patient and communication to the clearinghouse or other entity having a need to monitor and receive reports of patient compliance with the prescription. Other preferable and optional data that can be concatenated and or displayed on the display 190 with the average time interval 460 can also include a single digit count code that can be selected to be any of a number of possible 2-character or 3-character codes that can represent the number of unit doses dispensed, as well as a single character code that represents a true-false error reporting or other condition identifier code that can be used to identify whether the unit dose compliance monitoring and reporting device and system 100 experienced and or recorded any errors during use, and or whether any particular, predetermined unit dose of interest was dispensed.

The latter condition identifier code can more specifically be used to monitor and report whether the unit doses on the device and system 100 were dispensed in a preferred order of dispensing, whether a first unit dose, intermediate unit dose, and or last unit dose was dispensed in an preferred order, or whether such were dispensed at all. This latter configuration can be particularly useful for monitoring and reporting dispensement of sequence sensitive medicament such as steroid unit doses that diminish or increase in concentration through the sequence of unit doses.

This alternative arrangement is also particularly well-suited for birth control and other hormone therapies that require dispensement of unit dose sequences wherein each unit dose may be different from the last and the next. Such additionally preferred and optional condition identifier codes can also be employed to augment the available information to be monitored, collected and reported in the unit dose compliance monitoring and reporting device and system 100 that are directed for use in prescription regimens wherein unit doses are to be dispensed over varying time intervals such that the previously contemplated and described average time interval 460 may be most useful for monitoring and reporting compliance in a way that identifies whether the patient generally or specifically complied with the requirement to consume the unit doses of medicament at the prescribed, non-equal time intervals.

Preferably, the preceding time/date data 450 as well as the manufacturer and medicament product identification data is displayed on the display 190 of the device and system 100 in the form of an encoded inbound report code 470 that is an alphanumeric sequence of characters, which is embedded with the encoded information. Such contemplated encoded information can include any of the previously described codes including the proposed condition identifier codes.

Although such an inbound report code can be implemented in many suitable configurations, one particularly useful form of such a code 470 preferably enabled as an alphanumeric sequence of characters limited to the English alphabet of the 26 uppercase letters "A" through "Z" and combined with the 9 Arabic numeral digits "1" through "9". A similarly restricted character set is contemplated for embodiments of the instant inventive inbound report code 470 that are embodied for use in other non-English alphabets including, for purposes of example without limitation, Arabic, Cyrillic, Greek, Hebrew, Sanskrit, traditional and simplified Chinese, and a host of other main stream alphabets.

With this particular English alphanumeric configuration, each character in the sequence of characters that establish a certain predetermined inbound report code 470 can be selected from a group of 35 such characters in the English alphabet and Arabic numeral-based languages. Thus, those skilled in the relevant arts may be able to appreciate that each added character of the sequence of characters of the contemplated inbound report code 470 will increase the possible number of uniquely distinct inbound report codes 470.

More specifically, for applications of the inventive unit dose compliance monitoring and reporting device and system 100 that incorporates the myriad possible variations of inbound report codes 470, a code 470 having sequence of 2 characters based upon the 35 available alphanumeric characters creates 35×35 or 1,225 possible unique inbound report codes 470 having such combinations of characters. Similarly, a 3 character inbound reporting code will enable 35×35×35 or 42,875 possible unique inbound report codes 470. Further, 5 characters enables over 52,000,000 unique codes 470, and 8 characters creates over 2.25 trillion available unique inbound report codes 470.

More importantly, since the patient using the inventive device and systems 100 of the instant invention must read and communicate such inbound report codes 470 to establish the monitoring and reporting capabilities of the instant invention, is it preferable to limit the number of characters that must be communicated by the patient. Thus, in one of the preferred embodiments of the unit dose compliance monitoring and reporting device and system 100 of the invention, the inbound report code 470 is preferably or optionally selected to have a predetermined number of characters in the sequence that is 8 such alphanumeric characters.

This inbound report code 470 and other information is then reported to a clearinghouse through any number of possibly desirable means of communication 480, which can include telephone, internet, facsimile, and other means such as those described in FIG. 7. The clearinghouse or recipient of the inbound report code 470 validates the information, confirms and creates any needed additional patient inquiry and or inquiries 495 regarding the expected compliance, and forwards it to those entities 500 with an interest or concern in monitoring and analyzing 510 patient compliance 440 with the prescription 420, 430.

In circumstances where additional information may be needed from the patient to ascertain additional facts and circumstances concerning compliance, the contemplated inquiry request 495 can be automatically communicated back to the patient via the means by which the patient communicated compliance information to the clearinghouse, or any other preferred methods of communication contemplated hereby. Additionally and or alternatively, such compliance inquiries can be directed to the manufacturer, the retail pharmacy, and any other interested individual and or entity. This function is especially useful in applications where a recall may have been implemented, but where a patient was unadvised. In this circumstance, the patient reports consumption via the compliance system and the entities and individuals most interested in addressing the recall issues and concerns can effectively follow up with the patient to ensure any remaining medicaments are recalled from the patient. Such entities and individuals most interested include, for purposes of example but no for purposes of limitation, the treating physician or other prescribing healthcare professional, the prescription dispensing entity or retail pharmacy, the manufacturer, the distributor, a state or federal government organization, the medical professional department of the health care insurer carrier, and any other individual or entity that may be involved in patient treatment, compliance monitoring, and medicament control and tracking.

As noted, such entities 500 can typically or particularly include health care insurance companies seeking to control patient prescription drug costs by giving patients an incentive to comply with the clinical prescription requirements. One contemplated incentive includes withholding reimbursement and payment for the prescription drug prescribed for and consumed by the patient until the patient consumes some predetermined quantity of prescribed unit doses. Using the novel and new unit dose compliance monitoring and reporting device and system 100, the patient consumes all of the unit doses incorporated on the device 100 and the device automatically monitors time intervals and other conditions, and reports and displays compliance information that the patient can then readily communicate to the interested entity 500.

As noted, such compliance information can be minimal to ease the burden on the patient, and can further include more detailed information as preferred by the parties that adopt and implement the device and system 100. More particularly, such minimal information can include perhaps only an average time interval 460, which may be sufficient information for the interested entity to confirm compliance. In the alternative, more information can also be reported when patient compliance must be ascertained with resolution that is more definitive. In such circumstances, the time/date data 450 can be displayed for reporting by scrolling through the information displayed on the display 190 using the user interface features 210. Further, more limited data can be displayed and reported, which data can be algorithmically encoded or embedded in the form of the contemplated inbound report code 470, which can incorporate the average time interval 460 as well as the perhaps, for purposes of illustrative example without limitation, the manufacturer information.

Numerous alterations, modifications, and variations of the preferred embodiments disclosed herein would be apparent to those skilled in the art and they are all contemplated to be within the spirit and scope of the instant invention, which is limited only by the following claims. For example, although specific embodiments have been described in detail, those with skill in the art can understand that the preceding embodiments and variations can be modified to incorporate various types of substitute and/or additional materials, components, relative arrangements of components, features, elements, and dimensional configurations for compatibility with the wide variety of possible applications that are susceptible for use with the inventive unit dose compliance monitoring and reporting device according to the principles of the instant invention. Accordingly, even though only few such embodiments, alternatives, variations, and modifications of the present invention are described herein, it is to be understood that the practice of such additional modifications and variations and the equivalents thereof, are within the spirit and scope of the invention as defined in the following claims.

I claim:

1. A unit dose medication compliance monitoring and reporting device, comprising:
 a dispenser shell with a dispensing face and defining a plurality of unit dose containers, each container defining an opening through the dispensing face;
 a retainer sheet configured to be confrontingly affixed to the dispensing face to seal each container opening and to burst proximate to each opening as the unit dose is dispensed through the respective openings of the containers;
 a sensor network arranged about the retainer sheet to have a plurality of frangible electrical container integrity signal paths, each path being positioned to substantially extend across a respective opening when the retainer sheet is affixed;
 a monitoring and reporting circuit in electrical communication with timer and memory circuits, which are configured to record a time signal at each instance when a one of the frangible signal paths is interrupted as the unit dose is dispensed, the monitoring and reporting circuit being further adapted to compute and record an average time interval signal of the recorded time signals; and
 a data display device in electronic communication with the monitoring and reporting circuit and configured to communicate data that includes the average time interval signal of the recorded time signals.

2. The unit dose medication compliance monitoring and reporting device according to claim 1, further comprising:
 a user data interface in electronic communication with the monitoring and reporting circuit proximate to the data display and being adapted to selectively adjust the data displayed.

3. The unit dose medication compliance monitoring and reporting device according to claim 1, wherein the monitoring and reporting circuit is further adapted to count and to communicate to the data display a number signal representing the unit doses dispensed.

4. The unit dose medication compliance monitoring and reporting device according to claim 1, wherein the monitoring and reporting circuit is further adapted to, after the last unit dose is dispensed, store and to communicate to the data display a signal that embodies the average time interval signal, the doses dispensed signal, and a signal that represents an inbound report code; and
 wherein the signals and the inbound report code are communicated to a clearinghouse for automated validation and compliance reporting and monitoring.

5. The unit dose medication compliance monitoring and reporting device according to claim 1, wherein the monitoring and reporting circuit is further adapted to store and to alternately communicate to the data display a doses remaining quantity signal and a prescription regimen signal.

6. The unit dose medication compliance monitoring and reporting device according to claim 1, further comprising:
 an energy source in electrical communication with the monitoring and reporting circuit and the data display, the energy source adapted to energize the monitoring and reporting circuit and data display after a first unit dose is dispensed.

7. The unit dose medication compliance monitoring and reporting device according to claim 6, wherein the energy source is a photovoltaic power supply.

8. The unit dose medication compliance monitoring and reporting device according to claim 1, wherein the retainer sheet incorporates a plurality of sandwiched layers that include a sealing layer adapted to substantially prevent passage of liquids, gases, and solids, a conductor layer configured to receive the sensor network, a metallic layer, and an insulative layer between the metallic and conductor layers.

9. The unit dose medication compliance monitoring and reporting device according to claim 8, wherein the conductor layer is treated with a conductive substance in a circuit pattern that establishes the sensor network, and that includes a sensor network interface, the conductor layer also being adapted with grounding bosses in electronic communication with the metallic layer.

10. A unit dose medication compliance monitoring and reporting blister pack, comprising:
 a dispenser shell with a dispensing face and defining a plurality of unit dose containers, each container defining an opening through the dispensing face;
 a retainer sheet configured to be confrontingly affixed to the dispensing face to seal each container opening and to burst proximate to each opening as the unit dose is dispensed through the respective openings of the containers;
 a sensor network arranged about the retainer sheet and dispenser shell to have a plurality of frangible electrical container integrity signal paths, each path being positioned to substantially extend across a respective opening when the retainer sheet is affixed;

a monitoring and reporting circuit carried from respective extended edges of the dispenser shell and retainer sheet, and in electrical communication with timer and memory circuits, which monitoring and reporting circuit is configured to record to the memory circuit a time signal of the timer circuit at each instance when a one of the frangible signal paths is broken as the unit dose is dispensed, the monitoring and reporting circuit being further adapted to compute and record an average time interval signal from the recorded time signals; and a data display device carried from the respective extended edges and in electronic communication with the monitoring and reporting circuit to display data that includes the average time interval signal of the recorded time signals.

11. The unit dose medication compliance monitoring and reporting blister pack according to claim 10, wherein the monitoring and reporting circuit counts and communicates to the data display a signal that represents a number of the unit doses dispensed.

12. The unit dose medication compliance monitoring and reporting blister pack according to claim 11, wherein after the last unit dose is dispensed, the monitoring and reporting circuit stores and communicates to the data display a signal representing the doses dispensed signal, the average time interval signal, and an inbound report code; and wherein the signals and the inbound report code are communicated to a clearinghouse for automated validation and compliance reporting and monitoring.

13. The unit dose medication compliance monitoring and reporting blister pack according to claim 10, wherein the monitoring and reporting circuit stores and alternately communicates to the data display a doses remaining quantity signal and a prescription regimen signal.

14. The unit dose medication compliance monitoring and reporting blister pack according to claim 10, further comprising:

an energy source in electrical communication with the monitoring and reporting circuit and the data display, which energizes the circuit and display after a first unit dose is dispensed.

15. The unit dose medication compliance monitoring and reporting blister pack according to claim 14, wherein the energy source is a photovoltaic power supply.

16. The unit dose medication compliance monitoring and reporting blister pack according to claim 10, wherein the retainer sheet incorporates a plurality of sandwiched layers that include a sealing layer that substantially prevents passage of liquids, gases, and solids, a conductor layer that incorporates the sensor network, a metallic layer, and an insulative layer between the metallic and conductor layers.

17. The unit dose medication compliance monitoring and reporting blister pack according to claim 16, wherein the conductor layer includes a patterned conductive substance that forms a part of the sensor network and that includes a sensor network interface, the conductor layer also incorporating grounding bosses in electronic communication with the metallic layer.

18. A unit dose medication compliance monitoring and reporting apparatus, comprising:

a dispenser pack with an aperture face and defining a plurality of blister compartments sized to contain respective unit doses, each blister compartment defining a recess with an opening in the aperture face;

a retainer sheet configured to be confrontingly affixed to the aperture face to seal each opening and to burst proximate thereto as the unit dose is dispensed;

a dispensement sensing network arranged about the retainer sheet to have a plurality of frangible electrical signal paths that are interrupted upon respective dispensement, each signal path arranged to substantially extend across a respective opening when the retainer sheet is affixed;

a monitoring and reporting circuit with timer and memory circuits, which are configured to record a time signal at each instance when a one of the frangible signal paths of the plurality is interrupted as the unit dose is dispensed, the monitoring and reporting circuit being further adapted to count each unit dose dispensed and to compute and store an average time interval from the recorded time intervals each time a new time signal is recorded; and a data display device in electronic communication with the monitoring and reporting circuit and configured to display data that includes the average time interval signal of the recorded time signals.

19. The unit dose medication compliance monitoring and reporting apparatus according to claim 18, wherein the monitoring and reporting circuit is further configured to, after the last unit dose is dispensed, store and to communicate to the data display a signal that embodies the average time interval signal, the count of doses dispensed, and an inbound report code; and wherein the signals and the inbound report code are communicated to a clearinghouse for automated validation and compliance reporting and monitoring.

20. The unit dose medication compliance monitoring and reporting apparatus according to claim 18, wherein the retainer sheet incorporates a plurality of sandwiched layers that include a sealing layer that substantially prevents passage of liquids, gases, and solids, a conductor layer that incorporates the sensor network, a metallic layer, and an insulative layer between the metallic and conductor layers; and wherein the conductor layer includes a patterned conductive substance that forms a part of the sensor network and that includes a sensor network interface, the conductor layer also incorporating grounding bosses in electronic communication with the metallic layer.

* * * * *